United States Patent
Shah

(10) Patent No.: US 10,405,552 B2
(45) Date of Patent: Sep. 10, 2019

(54) COMPOSITE INSECTICIDAL COMPOSITION

(71) Applicant: S. C. Johnson & Son, Inc., Racine, WI (US)

(72) Inventor: Bhaveshkumar Shah, Kenosha, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 15/601,393

(22) Filed: May 22, 2017

(65) Prior Publication Data

US 2018/0332854 A1 Nov. 22, 2018

(51) Int. Cl.
*A01N 53/00* (2006.01)

(52) U.S. Cl.
CPC .................................. *A01N 53/00* (2013.01)

(58) Field of Classification Search
CPC ........ A01N 53/00; A01N 25/04; A01N 25/06; A61Q 17/02
See application file for complete search history.

(56) References Cited

U.S. PATENT DOCUMENTS

| | | | |
|---|---|---|---|
| 5,091,183 A | 2/1992 | Yano et al. | |
| 2006/0182774 A1* | 8/2006 | Fujii | A01M 1/2038 424/405 |
| 2009/0263511 A1* | 10/2009 | Shah | A01N 65/00 424/725 |

FOREIGN PATENT DOCUMENTS

| | | | | |
|---|---|---|---|---|
| CN | 104522040 | | 4/2015 | |
| EP | 0125471 | A2 | 11/1984 | |
| EP | 0320908 | B1 | 7/1991 | |
| EP | 0370321 | B1 | 3/1993 | |
| EP | 0591195 | A1 | 4/1994 | |
| EP | 0401336 | B1 | 4/1995 | |
| EP | 0656411 | A1 | 6/1995 | |
| EP | 0771526 | A2 | 5/1997 | |
| EP | 0823213 | B1 | 2/1998 | |
| EP | 0859035 | A1 | 8/1998 | |
| EP | 0805625 | B1 | 5/2000 | |
| EP | 0915657 | B1 | 1/2002 | |
| EP | 0857019 | B1 | 12/2002 | |
| EP | 0907317 | A1 | 1/2003 | |
| EP | 0855858 | B1 | 3/2003 | |
| EP | 0962135 | B1 | 3/2003 | |
| EP | 0946090 | B1 | 4/2003 | |
| EP | 1003369 | B1 | 5/2003 | |
| EP | 1071323 | B1 | 7/2004 | |
| EP | 1250043 | B1 | 9/2004 | |
| EP | 1269842 | B1 | 10/2004 | |
| EP | 1298995 | B1 | 2/2006 | |
| EP | 1337146 | B1 | 2/2006 | |
| EP | 1661458 | A1 | 5/2006 | |
| EP | 1657979 | B1 | 12/2006 | |
| EP | 1249482 | B1 | 7/2007 | |
| EP | 1865776 | A1 | 12/2007 | |
| EP | 1929864 | A1 | 6/2008 | |
| EP | 2061311 | A2 | 5/2009 | |
| EP | 2061312 | A2 | 5/2009 | |
| EP | 2406044 | A1 | 1/2012 | |
| EP | 2424347 | A1 | 3/2012 | |
| EP | 2424370 | A2 | 3/2012 | |
| EP | 2470007 | A2 | 7/2012 | |
| EP | 2382351 | B1 | 10/2012 | |
| EP | 2581431 | A1 | 4/2013 | |
| EP | 2139336 | B1 | 5/2013 | |
| EP | 2585118 | A1 | 5/2013 | |
| EP | 2708126 | A1 | 3/2014 | |
| EP | 2259683 | B1 | 4/2014 | |
| EP | 2729188 | A1 | 5/2014 | |
| EP | 2747556 | A2 | 7/2014 | |
| EP | 1382399 | B1 | 9/2015 | |
| EP | 2482665 | B1 | 11/2015 | |
| WO | 96/32843 | A2 | 10/1996 | |
| WO | WO 2006111750 | A1 * | 10/2006 | ............. A01N 25/06 |
| WO | WO 2010084301 | A1 * | 7/2010 | ............. A01N 25/06 |
| WO | 2013/010099 | A1 | 1/2013 | |
| WO | 2014040720 | A1 | 3/2014 | |
| WO | 2015/133318 | A1 | 9/2015 | |
| WO | 2015159772 | A1 | 10/2015 | |

OTHER PUBLICATIONS

Yan et al. (Journal of Pharmaceutical and Biomedical Analysis, 2010, vol. 51, lines 774-777) (Year: 2010).*
International Search Report and Written Opinion issued in International Application No. PCT/US2018/033322, dated Jul. 20, 2018, 14 pages.
"Registered Pesticides List—Part I," Chemwatch. Net, Apr. 20, 2016, pp. 1-7, XP055491433, Retrieved from the Internet: URL: http://full.chemwatch.net/galleria/LEGSREGS/30-2-4-8-852-3-AA-20160420.pdf [retrieved on Jul. 10, 2018].
Yan et al., "Simultaneous determination of nine pyrethroids in indoor insecticide products by capillary gas chromatography," Journal of Pharmaceutical and Biomedical Analysis, vol. 51, Issue 3, Feb. 5, 2010, pp. 774-777.

* cited by examiner

*Primary Examiner* — Mark V Stevens
(74) *Attorney, Agent, or Firm* — Quarles and Brady LLP

(57) ABSTRACT

A composite insecticidal composition is disclosed that contains three active ingredients, which are transfluthrin, prallethrin, and cypermethrin. The composite insecticide composition may further contain at least one of a solvent and a propellant. The weight percentage of each of the active ingredients may be about 0.05% to 0.5%.

22 Claims, No Drawings

COMPOSITE INSECTICIDAL COMPOSITION

CROSS REFERENCE TO RELATED APPLICATIONS

Not applicable.

REFERENCE REGARDING FEDERALLY SPONSORED RESEARCH OR DEVELOPMENT

Not applicable.

SEQUENCE LISTING

Not applicable.

BACKGROUND

1. Technology Field

The present disclosure relates to a composite insecticidal composition and, more particularly, to an aerosol composite insecticidal composition, that comprises at least three active ingredients and is effective against both flying and crawling insects.

2. Description of the Background

Insecticide has been used over the years to prevent insects from attacking humans, animals, and crops. Diseases transmitted by insects are a major health hazard. Insects (mosquitoes, flies, and the like) transmit a number of diseases caused by the exposure of the victim to infectious agents such as viruses (chikungunya virus, yellow fever, dengue fever, etc.), bacteria (Lyme disease, plague, etc.), and parasites (malaria, sleeping sickness, leishmaniasis, filariasis, etc.) carried by the insect.

For example, flying insects, such as mosquitoes, cause greater human suffering than any other organism—over one million people worldwide die from mosquito-borne diseases annually. Not only can mosquitoes carry diseases that afflict humans, they also transmit several diseases and parasites that affect other animals, such as dogs and horses. These include dog heartworm, West Nile virus (WNV), and Eastern equine encephalitis (EEE). In addition, mosquito bites may cause severe skin irritation resulting from an allergic reaction to the mosquito's saliva, causing inflammation and itching at the affected site, leading to the possible introduction of other disease causing agents.

Crawling insects, such as ants and cockroaches, are responsible for health problems as well. Cockroaches in the home environment are a health hazard not only because of the risks posed by cockroach antigens to asthma sufferers, but also because they can carry disease-causing agents. Cockroaches may play a role as carriers of intestinal diseases, such as diarrhea, dysentery, typhoid fever and cholera.

Known commercially available insecticides are typically effective against either flying insects or crawling insects, but not both. Therefore, it is desirable to have a composite insecticidal composition with the ability to knockdown and kill both flying and crawling insects in a quick, efficient manner, be available in a single product, and to further provide residual activity.

SUMMARY

Embodiments of the current disclosure describe a composite insecticidal composition comprising transfluthrin, prallethrin, and cypermethrin. In certain embodiments the transfluthrin is present at about 0.05% to about 0.5% by weight; the prallethrin at about 0.05% to about 0.5% by weight; and the cypermethrin at about 0.05% to about 0.5% by weight.

In certain embodiments, the transfluthrin is present at about 0.1% by weight; the prallethrin at about 0.1% by weight; and the cypermethrin at about 0.1% by weight.

In certain embodiments, the composite insecticidal composition further comprises at least one of a solvent and a propellant. The solvent may comprise aliphatic $C_9$-$C_{14}$ hydrocarbons, alicyclic $C_9$-$C_{14}$ hydrocarbons, naphtha, petroleum distillate, paraffins, iso-paraffins, isoparaffinic hydrocarbons, cyclopraraffins, alkanes, iso-alkanes, cycloalkanes, and the like, and any combinations thereof. The propellant may comprise methane, ethane, propane, pentane, isobutene, N-butane, iso-butane, dimethyl ether, 1,1-difluoroethane, 1,1,1,2-tetrafluoroethane, carbon dioxide, nitrogen, air, and the like, and any combinations thereof. In certain embodiments, the composite insecticidal composition is a composition for killing insects, comprising between about 0.05 and 0.5% by weight of transfluthrin, between about 0.05 and 0.5% by weight of prallethrin, between about 0.05 and 0.5% by weight of cypermethrin, between about 10 and 90% by weight of a petroleum distillate solvent or an isoparaffinic hydrocarbon solvent or both, and between about 10 and 80% by weight of a propellant. Certain embodiments comprise a method of killing insects, the method comprising providing the composition of claim 1 in a dispenser which dispenses the composition at a rate of between about 2.0 gram/second and about 3.5 gram/second, and instructing a user to spray the composition for a duration of between about 4 and about 5 seconds.

DETAILED DESCRIPTION OF THE INVENTION

A composite insecticidal composition designed to knockdown and kill both flying and crawling insects more effectively than other known compositions is presently disclosed. In the pest control field, it is known that households tend to suffer from both flying and crawling insects. Therefore, it is important to develop an insecticidal composition that can knockdown and/or kill both flying and crawling insects in a timely fashion. It has been found that an insecticidal composition comprising three actives may provide such a benefit.

In certain embodiments, the composite insecticidal composition comprises transfluthrin, prallethrin, and cypermethrin. Transfluthrin is a fast-acting pyrethroid insecticide with low persistency. It has the molecular formula $C_{15}H_{12}C_{12}F_4O_2$. Prallethrin is another pyrethroid insecticide, which has the molecular formula $C_{19}H_{24}O_3$.

Cypermethrin is a synthetic pyrethroid used as an insecticide in large-scale commercial agricultural applications as well as in consumer products for domestic purposes. It behaves as a fast-acting neurotoxin in insects. It is easily degraded in soil and on plants but can be effective for weeks when applied to indoor inert surfaces, providing long residual activity. Cypermethrin has a molecular formula of $C_{22}H_{19}Cl_2NO_3$.

In determining a concentration of each of the active ingredients, the type of active ingredients, the spray rate of the composition, and the instructions regarding use of the composition are considered. In some embodiments, the spray rate of the active ingredients is in the range of about 2.0 grams per second to about 2.5 grams per second. In other embodiments, the spray rate of the active ingredients is in the range of about 2.5 grams per second to about 3.0 grams per second. In yet other embodiments, the spray rate of the active ingredients is in the range of about 3.0 grams per second to about 3.5 grams per second. In some embodiments the user instructions for aerosol compositions may instruct the user to spray for about 4 to about 5 seconds. In other embodiments, users are instructed to spray for about 5 to about 8 seconds. In yet other embodiments, users are instructed to spray for about 8 to about 12 seconds.

It is desirable to provide an insecticidal composition comprising a particular amount of active ingredient to reach its best efficacy (ability to kill or knock down pests) when a certain spray rate and a certain amount of spray time (spray duration) are used. In certain embodiments, the transfluthrin is about 0.05% to about 0.5% by weight, the prallethrin is about 0.05% to about 0.5% by weight, and the cypermethrin is about 0.05% to about 0.5% by weight. In accordance with an exemplary embodiment, the transfluthrin is about 0.1% by weight, the prallethrin is about 0.1% by weight, and the cypermethrin is about 0.1% by weight. In some embodiments, the particular weight percentage may vary, but each of the transfluthrin, prallethrin, and cypermethrin are equal in their particular weight percentage to one another. In other embodiments, regardless of whether the three components are equal to one another, the weight percentage of each component is at least about 0.1%, or less than or equal to about 0.5%, or greater than or equal to about 0.05%. While specific values chosen for this embodiment are recited, it is to be understood that, within the scope of the disclosure, the concentrations of all the active ingredients may vary to suit different applications. The concentration ranges of active ingredients are associated not only with the type of active ingredient, but with spray rate and instructions for use, including, but not limited to, spray duration and/or recommended proximity to the pest.

EXAMPLES

Peet-Grady chambers were used in the studies conducted on mosquitoes and also on *Periplaneta americana* and *Blatella germanica* cockroaches. About 2.5 to about 3.5 grams of each test substance was sprayed into the chamber and mortality was observed 60 minutes after spraying of the test substances. In the first 10 minutes of observing the mortality, the number of falling mosquitoes or cockroaches was recorded at one minute intervals. After the first 10 minutes, the number of falling mosquitoes or cockroaches was recorded at 10 minute intervals up until 60 minutes. Following the first 60 minutes of the mortality observation, all the tested mosquitoes were moved outside the chambers and placed in a room. The number of falling mosquitoes was recorded every hour until the sixth hour. After 24 hours of observation, the number of mosquitoes that can revive and become active again was also recorded. Similarly, the number of falling cockroaches was recorded every hour until the sixth hour and at 24 hours. Studies were conducted at two testing locations.

Composition 1 according to an embodiment of the present disclosure comprises about 0.1% by weight cypermethrin, about 0.1% by weight transfluthrin, about 0.1% by weight prallethrin, about 29% to about 29.7% by weight isoparaffinic hydrocarbon solvent and about 70% by weight propellant. The average knockdown of *Culex quinquefasciatus* (southern house mosquito) after exposure to Composition 1 for 1 minute is about 3.5%, for 2 minutes about 21%, for 3 minutes about 38.5%, for 4 minutes about 54%, for 5 minutes about 67%, for 6 minutes about 79.5%, for 7 minutes about 86.5%, for 8 minutes about 93%, and for 9 minutes about 98%. Exposure to Composition 1 reaches about 100% knockdown of the southern house mosquito in about 10 minutes, which is significantly faster in comparison to other known compositions. Further, Composition 1 has a faster and higher knockdown rate of the southern house mosquito over any other tested formulations, except for Formula 1. After 24 hours exposure to Composition 1, about 99.5% of the southern house mosquitoes were killed.

According to EPA standards, a "dead" (or killed) insect must be an insect with absolutely no movement, no twitching, no antenna moving, etc. A dead insect is probed or subjected to other stimuli to verify lack of movement. A "knockdown" of an insect is considered to be any condition between dead and full mobility, i.e., knockdown is often measured as the insect's inability to respond to a stimulus such as light or touch. For mosquitos, knockdown is defined as mosquitoes resting on the floor of the chamber and experiencing some aberrant behavior, such as on laying on their back or side, spinning erratically in one spot, or the inability to sustain normal flight more than a few inches giving an impression of hopping. Especially when actual mortality rate may be difficult to assess, knockdown is used to measure the effect of a pesticide. It is desirable to not only knockdown, but to kill insects to avoid the breeding of knockdown resistant insects. Knockdown resistance ("kdr"), describes cases of resistance to diphenylethane (e.g. DDT) and pyrethroid insecticides in insects and other arthropods that result from reduced sensitivity of the nervous system caused by point mutations in the insect's genetic makeup. Such mutative resistance is characterized by the presence of kdr alleles in the insect's genome. Knockdown resistance remains a threat to the continued usefulness of pyrethroids in the control of many pest species. As such, it is desirable to have a composite insecticidal composition capable of not only insect knockdown but also insect death.

The average knockdown of southern house mosquitoes after exposure to Composition 1 for 1 minute is about 9.3%, for 2 minutes about 20.7%, for 3 minutes about 36.7%, for 4 minutes about 47.3%, for 5 minutes about 63.3%, for 6 minutes about 76.7%, for 7 minutes about 78%, for 8 minutes about 86.7%, for 9 minutes about 90%, and for 12 minutes about 98.7%. Exposure to Composition 1 reaches 100% knockdown of the southern house mosquito in about 13 minutes, significantly faster in comparison to other known compositions. After 24 hours exposure to Composition 1, 100% of the southern house mosquitoes were killed. Further, Composition 1 has a faster and higher knockdown rate of the southern house mosquito than any other tested formulations. The average of knockdown of *Aedes aegypti* (yellow fever mosquito) after exposure to Composition 1 for 1 minute is about 77% and for 2 minutes about 93%. Exposure to Composition 1 reaches 100% knockdown of the yellow fever mosquito in just 3 minutes, significantly faster in comparison to other known compositions. Further, Composition 1 has a faster and higher knockdown rate of the yellow fever mosquitos than any other tested formulation.

Composition 1 is also effective against crawling insects, such as *Periplantea americana* (American cockroach) and *Blatella germanica* (German cockroach).

The average knockdown of American cockroaches following space spray exposure to Composition 1 for 1 minute is about 4%, for 2 minutes about 27.2%, for 3 minutes about 40%, for 4 minutes about 77.6%, for 5 minutes about 88%, for 6 minutes about 92.8%, for 7 minutes about 94.4%, for 8 minutes about 95.2%, and for 9 minutes about 96%. Exposure to Composition 1 reaches 100% knockdown of American cockroaches in about 10 minutes, which is significantly faster in comparison to other known compositions. After 24 hours exposure to Composition 1, about 20.8% of American cockroaches were killed.

The average knockdown of German cockroaches following space spray exposure to Composition 1 for 1 minute is about 89.6% and reaches about 100% in 2 minutes. After 24 hours exposure to Composition 1, about 68% of German cockroaches were killed, which is the highest kill rate compared to other tested formulations.

The average knockdown of American cockroaches following direct spray exposure to Composition 1 for 1 minute is about 59%, for 2 minutes about 84%, for 3 minutes about 96%, and reaches 100% in just about 4 minutes. Composition 1 has a faster and higher knockdown rate of American cockroaches than any other tested formulation.

Further, the average knockdown of German cockroaches after direct spray exposure to Composition 1 for 1 minute is about 72%, for 2 minutes about 44%, and reaches 100% in about 3 minutes. Composition 1 has a faster and higher knockdown rate of German cockroaches than any other tested formulation.

The currently disclosed composite insecticidal composition exhibits faster and higher knockdown rates and higher killing rates against flying insects and crawling insects compared to other tested formulations. Other formulations, including other commercially available formulations, may have only fast and high knockdown rates against either flying insects or crawling insects, but not both. The currently disclosed composite insecticidal composition is the only composition known that is effective against both flying and crawling insects at the rates and times disclosed herein.

Table 1 provides a comparative study with other tested insecticidal formulations. All Peet-Grady Data is generated from label usage dosage of 1.8 seconds except for Composition 1 (0.90 second dose), and all direct spray knockdown data is generated using a 1.0 second dose from 18 inches unless noted with an asterisk (*).

TABLE 1

Comparative Study of Composition 1 and Other Insecticidal Formulations

| All Values Expressed in % by wt. | Housefly Peet-Grady | Mosquito Peet-Grady | German cockroach Direct Spray | American cockroach Direct Spray | Carpenter Ant Direct Spray |
|---|---|---|---|---|---|
| Composition 1 Prallethrin 0.1% Cypermethrin 0.1% Transfluthrin 0.1% | Mean KT90 5.38 min | Aedes aegypti mean KT90 2.78 min Culex mean KT90 2.75 min Anopheles mean KT90 2.74 min Aedes albopictus mean KT90 2.84 min | Mean KT90 27.6 sec | Mean KT90 177 sec | Mean KT90 30.6 sec |
| Formulation A d-Phenothrin 0.125% Prallethrin 0.1% | Mean KT90 6.02 min | Aedes aegypti mean KT90 4.61 min Culex mean KT90 4.60 min Anopheles mean KT90 4.61 min | Mean KT90 36.53 sec *0.5 second dose | Mean KT90 166.8 sec | 100% KD at 5 min |
| Formulation B Cypermethrin 0.1% Imiprothrin 0.031% Prallethrin 0.03% | Mean KT90 7.89 min | Aedes aegypti mean KT90 4.93 min Culex mean KT90 6.23 min Anopheles mean KT90 4.62 min | Mean KT90 16.20 sec *0.5 second dose | Mean KT90 55.2 sec | 100% KD at 5 min |
| Formulation C Imiprothrin 0.05% Prallethrin 0.05% Cyfluthrin 0.015% | Mean KT90 13.42 Min | Aedes aegypti mean KT90 11.01 Min Culex mean KT90 10.01 Min Anopheles mean KT90 9.07 min Aedes albopictus mean KT90 13.09 min | 100% KD at 30 Sec | 100% KD at 30 Sec | Mean KT90 65 sec |
| Formulation D Imiprothrin 0.05% Cyfluthrin 0.015% | Mean KT90 8.09 min | Aedes aegypti mean KT90 11.74 min Culex mean KT90 12.36 Min Anopheles mean KT90 13.39 Min | Mean KT90 10.08 sec *0.5 gram dose | Mean KT90 62.10 sec *1.0 gram dose | 100% KD at 5 min |
| Formulation E d-Phenothrin 0.125% Prallethrin 0.1% | Mean KT90 7.59 min | Aedes aegypti mean KT90 4.60 min Culex mean KT90 4.91 Min Anopheles mean KT90 4.59 Min Aedes albopictus mean KT90 4.71 Min | Mean KT90 42.80 sec *0.5 second dose | Mean KT90 122.7 sec | 100% KD at 5 min |

TABLE 1-continued

Comparative Study of Composition 1 and Other Insecticidal Formulations

| All Values Expressed in % by wt. | Housefly Peet-Grady | Mosquito Peet-Grady | German cockroach Direct Spray | American cockroach Direct Spray | Carpenter Ant Direct Spray |
|---|---|---|---|---|---|
| Formulation F d-Phenothrin 0.125% Prallethrin 0.1% | Mean KT90 4.83 min | Aedes aegypti mean KT90 4.60 Min Culex mean KT90 4.61 Min Anopheles mean KT90 4.56 min Aedes albopictus mean KT90 4.59 min | 92% KD at 5 min | 84% KD at 5 min | 100% KD at 5 min |
| Formulation G d-Tetramethrin 0.106% d-Phenothrin 0.098% Prallethrin 0.028% | Mean KT90 4.77 min | Aedes aegypti mean KT90 4.80 min Culex mean KT90 4.70 min Anopheles mean KT90 4.74 min Aedes albopictus mean KT90 4.67 min | Mean KT90 83.30 sec *0.5 second dose | Mean KT90 244.1 sec | NA |
| Formulation H d-Phenothrin 0.12% d-Tetramethrin 0.11% Prallethrin 0.05% | Mean KT90 8.92 min | Aedes aegypti mean KT90 6.45 min Culex mean KT90 7.47 min Anopheles mean KT90 8.93 min Aedes albopictus mean KT90 5.76 min | Mean KT90 88 sec | 92% KD at 300 sec | 100% KD at 5 min |

As depicted in Table 1, the efficacy data of Composition 1 compared to other testing substances (Formulations A-H) on houseflies and mosquitoes (*Aedes aegypti, Culex quinquefasciatus, Anopheles stephensi*, and *Aedes albopictus*) is generated using a Peet-Grady test chamber.

The test substance, Composition 1, was sprayed into the Peet-Grady test chamber for about 0.9 seconds in the presence of adult mosquitos and houseflies. The other test substances, such as Formulations A-H, were sprayed into the Peet-Grady test chamber for about 1.8 seconds in the presence of adult mosquitos and houseflies. The methodology provides a comparison using 0.9 seconds vs 1.8 seconds to demonstrate that Composition 1 in a 50% spray duration (0.9 seconds) performs better than the comparative formulations having a spray duration of 1.8 seconds. In other words, Composition 1 outperformed the comparative formulations, using only 50% of the spray duration of the comparative formulations.

Mosquito and housefly knockdown counts were taken at 3, 5, 10 and 15 minutes. Mortality counts were taken at 24±2 hours post treatment. Untreated control mosquitoes were set-up with knockdown counts taken at 15 minutes and mortality counts at 24±2 hours. The percent knockdown was calculated by comparing the number of mosquitoes that were introduced at the start of each test with those knocked-down at the specified intervals for both controls and treatments. The targeted weight of the test substances were recorded after spraying to determine the actual dosage. From the actual dose an active ingredient application rate was calculated. The discharge rate, R (grams per second), for the test substances (aerosol) was determined as:

Discharge rate($R$)=weight($D$)/Spray seconds($S$).

A container holding a testing substance was weighed after spraying and the difference was calculated ($D$) and the contents of the container were discharged into the spray hood for 5 seconds ($S$).

Mosquitoes were introduced to the testing chamber and were acclimated for approximately 1 minute. Prior to the treatment, the container including the test substances were weighed. The container was re-weighed after treatment. The weight of the test substances was measured after spraying to determine the actual dosage. Following mosquito acclimation, the test substances were sprayed into the chamber for about 0.9 seconds (Composition 1) or about 1.8 seconds (Formulations A-H). Immediately following the application the testing chamber was closed and the timer started. Knockdown counts were taken beginning approximately 30 seconds before the actual 3, 5, and 10-minute intervals. At approximately 14 minutes an exhaust on the chamber was opened. At approximately 15 minutes the downed mosquitoes were counted. To obtain a total mosquito count, the mosquitoes that were not knocked down were then collected and counted. Knockdown counts were taken at 15 minutes and 24-hour mortality counts at 24±2 hours.

With respect to the test results and referring to Table 1, the average time to reach 90% mortality (KT90) in houseflies when using Composition 1 was about 5.38 minutes, which is shorter than most KT90 of Formulations A-H, even though the spray durations of Formulations A-H were twice that of Composition 1. Further, the KT90 of each of the four different types of mosquitoes when using Composition 1 was much lower than the KT90 of each of Formulations A-H respectively, also with a spray duration twice that of Composition 1.

Referring to Table 1 again, the spray duration of studies conducted on German cockroaches, American cockroaches, and Carpenter ants was about 0.9 seconds for Composition 1 compared to about 1.8 seconds for Formulations A-H. Therefore, the amount of Composition 1 discharged during studies was about half of the amount discharged for each of the Formulations A-H. The average time to reach 90% mortality in German cockroaches for Composition 1 was about 27.6 seconds, which was shorter than most KT90 of Formulations A-H having a spray duration twice that of Composition 1. Further, the KT90 in Carpenter ants when using Composition 1 was about 30.6 seconds, which was shorter than the KT90 when using Formulations A-H, again having a spray duration twice that of Composition 1.

In certain embodiments, the composite insecticidal composition further comprises at least one of a solvent and a propellant. In other embodiments, the composite insecticidal composition may further comprise a fragrance. Such embodiments may comprise a fragrance at about 0.1% to about 2% by weight. In accordance with certain embodiments of the present disclosure, the composite insecticidal composition is an aerosol insecticidal composition, which is suitable for industrial and domestic applications. An embodiment comprises a dispensing container having aerosol dispensing means, at least three active ingredients, a solvent at a sufficient weight percentage to dissolve the active ingredients, and a propellant gas at a sufficient pressure to dispense the active ingredients dissolved in the solvent from the dispensing means as an aerosol. An aerosol insecticidal composition is ideal for use against both flying and crawling insects. For example, the aerosol composition may be sprayed in the air for any flying insect and may be sprayed in the air for preventative measures. For crawling insects, the aerosol composition may be sprayed directly on the insect or on inert surfaces such as, but not limited to, floorboards, under the sink, thresholds, and doorways as a preventative measure.

In certain embodiments, the solvent may be aliphatic $C_9$-$C_{14}$ hydrocarbons, alicyclic $C_9$-$C_{14}$ hydrocarbons, naphtha, petroleum distillate, paraffins, iso-paraffins, isoparaffinic hydrocarbons, cyclopraraffins, alkanes, iso-alkanes, cycloalkanes, and the like, and any combinations thereof. In certain embodiments the solvent is a petroleum distillate. In certain embodiments the petroleum distillate is comprised of hydrocarbons, $C_{11}$-$C_{14}$, n-alkanes, isoalkanes, cyclics, <2% aromatics. In certain embodiments the solvent is an isoparaffinic hydrocarbon. In certain embodiments the isoparaffinic hydrocarbon is naphtha (petroleum), hydrotreated heavy. In certain embodiments the solvent is comprised of a petroleum distillate or an isoparaffinic hydrocarbon or both. Certain embodiments may comprise at least two solvents. In certain embodiments the molar ratio of the at least two solvents may be in the range of about 1:1 to about 1:100 or about 1:100 to about 1:1 based on the total concentration of the solvents. In certain embodiments the solvent is present at an appropriate amount to dissolve the active ingredients, and may also contribute to carrier efficiency, which is defined as the degree to which a solvent induces penetration of an insecticide into the pest.

Petroleum distillates are commonly used to refer to aliphatic hydrocarbons, defined to also include natural or synthetic paraffinic hydrocarbons. Petroleum distillates may include mineral spirits, kerosene, white spirits, naphtha, Stoddard solvents, and the like. These products may contain trace amounts of benzene and/or other aromatics. Notwithstanding the non-limiting examples provided herein for solvents, other solvents, such as butylglycol, carbon tetrachloride, chloroform, chloropenthane, cresol, cyclohexanol, cyclohexanone, dibromomethane, 1,2-dichlorobenzene, 1,1-dichloroethane, 1,2-dichloroethane, dichloroethylene, 1,1-dichloroethylene, 1,2-dichloropropane, diethylbenzene, dimethyl carbonate, N,N-dimethylformamide, 1,4-dioxane, ethylbenzene, ethylene glycol, ethylglycol, formol, furfuryl alcohol, isophorone, isopropylglycol, kerosene, mesithyl oxide, mesithylene, methanol, 2-methoxypropanol, methylmetacrylate, methylcyclohexanol, methylcyclohexanone, methylglycol, methylisobuthylcarbinole, N-methylpyralidone, monochlorobenzene, nitrile acetic acid, nitrobenzene, 1-nitropropane, 2-nitropropane, oil of turpentine, O-chlorotoluene, pentachloroethane, phenol, propylbenzene, propylbromide, propyl chloride, propylene glycol, pyridine, styrene, tetrabenzylphenol, 1,1,2,2-tetrachloroethane, tetrachloroethylene, tetrahydrofuran, tetrahydronaphthalene, toluene, 1,1,1-trichloroethane, 1,1,2-trichloroethane, trichloroethylene, trimethylbenzene, vinyltoluene, xylene, and the like, or any combinations thereof, can also be used as the solvent. Certain solvents can increase the rate of penetration of contact insecticides through the insect cuticle.

In certain embodiments, the solvent is present at about 10% to about 90% by weight, preferably, about 25% to about 35% by weight. In a preferred embodiment, the solvent is present in about 30% by weight. While specific values of the solvent are chosen for this embodiment, it is to be understood that, within the scope of the disclosure, this value may vary over wide ranges to suit different applications. For example, the weight percentage of the solvent may increase to dissolve the active ingredients when, for example, there are additional active ingredients in one composition formula compared to another. The weight percentage of the solvent is balanced to effectively dissolve the active ingredients and effectively penetrate the cuticles of insects.

The propellant pressurizes the aerosol container and influences the form in which the composite insecticidal composition is discharged. The composition may be discharged in the form of foam, stream, or spray. The pressure normally created by the propellant is about 0.7 to about 9.8 bars (35 psi to 140 psi) at 21.1° C. If propellant concentration is increased, the composition may be discharged in the form of lower density foams. By adjusting the propellant and solvent used, quick breaking foams can be produced, or foams can be created that remain visually unchanged for days. To produce a spray, the propellant must have sufficient dispersive energy to overcome the surface tension of the liquid mixture, plus the cohesive and adhesive forces. For producing an aerosol product formulation, vapor pressure, spray characteristics, solubility, flammability, and corrosion are considered.

Aerosol propellants may comprise compressed gases, soluble gases, and liquefied gases. Many of these forms of aerosol propellants may be used in connection with the present disclosure. In some embodiments the propellant may be carbon dioxide, nitrogen, air, and the like, or any combinations thereof. In some embodiments, the propellant belongs to the liquefied gases category including, but not limited to hydrocarbon propellants. In certain embodiments, the propellant may be methane, ethane, propane, pentane, isobutene, N-butane, iso-butane, dimethyl ether, 1,1-difluoroethane, 1,1,1,2-tetrafluoroethane and the like, and any combinations of two or more thereof. In some embodiments, the propellant is propane. In other embodiments, the propellant is butane, including both N-butane and iso-butane.

Some embodiments may comprise at least a first propellant and a second propellant. In some embodiments the first and second propellants are in a molar ratio in the range of about 1:1 to about 100:1, or about 100:1 to about 1:1 based on the total concentration of the first and second propellant. In certain embodiments the first propellant is propane and the second propellant is butane.

Further, in certain embodiments, the propellant is present in about 0.5% to about 90% by weight, more preferably, about 10% to about 80% by weight. In a preferred embodiment, the propellant is present in about 70% by weight. While specific values chosen for the propellant are recited, it is to be understood that, within the scope of the disclosure, the value of this parameter may vary over wide ranges to suit different applications.

Any of the embodiments described herein may be modified to include any of the structures, compositions, or methodologies disclosed in connection with different embodiments.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A composition for killing insects comprising between about 0.05% to about 0.5% by weight of transfluthrin, between about 0.05% to about 0.5% by weight of prallethrin, between about 0.05% to about 0.5% by weight of cypermethrin, and a propellant; wherein the transfluthrin, the prallethrin, and the cypermethrin are the only pyrethroids in the composition.

2. The composition of claim 1, wherein:
the transfluthrin is about 0.1% by weight;
the prallethrin is about 0.1% by weight; and
the cypermethrin is about 0.1% by weight.

3. The composition of claim 1 further comprising a solvent.

4. The composition of claim 3, wherein the solvent is selected from the group consisting of aliphatic $C_9$-$C_{14}$ hydrocarbons, alicyclic $C_9$-$C_{14}$ hydrocarbons, naphtha, petroleum distillate, paraffins, iso-paraffins, isoparaffinic hydrocarbons, cycloparaffins, alkanes, iso-alkanes, cycloalkanes, and any combinations thereof.

5. The composition of claim 3, wherein the solvent is about 10% to about 90% by weight.

6. The composition of claim 5, wherein the solvent is about 25% to about 35% by weight.

7. The composition of claim 1, wherein the propellant is selected from the group consisting of methane, ethane, propane, pentane, isobutene, N-butane, isobutane, dimethyl ether, 1,1-difluoroethane, 1,1,1,2-tetrafluoroethane, carbon dioxide, nitrogen, air, and any combinations thereof.

8. The composition of claim 1, wherein the propellant is about 10% to about 80% by weight.

9. The composition of claim 8, wherein the propellant is about 70% by weight.

10. A composition for killing insects, comprising:
between about 0.05% to about 0.5% by weight of transfluthrin,
between about 0.05% to about 0.5% by weight of prallethrin,
between about 0.05% to about 0.5% by weight of cypermethrin,
solvent, and
propellant,
wherein the transfluthrin, the prallethrin, and the cypermethrin are equal in weight percentage and wherein the transfluthrin, the prallethrin, and the cypermethrin are the only pyrethroids in the composition.

11. The composition of claim 10, wherein:
the transfluthrin is about 0.1% by weight;
the prallethrin is about 0.1% by weight; and
the cypermethrin is about 0.1% by weight.

12. The composition of claim 10, wherein the solvent is selected from the group consisting of aliphatic $C_9$-$C_{14}$ hydrocarbons, alicyclic $C_9$-$C_{14}$ hydrocarbons, naphtha, petroleum distillate, paraffins, iso-paraffins, isoparaffinic hydrocarbons, cycloparaffins, alkanes, iso-alkanes, cycloalkanes, and any combinations thereof.

13. The composition of claim 10, wherein the solvent is about 25% to about 35% by weight.

14. The composition of claim 10, wherein the propellant is about 70% by weight.

15. The composition of claim 10, wherein the propellant is selected from the group consisting of methane, ethane, propane, pentane, isobutene, N-butane, isobutane, dimethyl ether, 1,1-difluoroethane, 1,1,1,2-tetrafluoroethane, carbon dioxide, nitrogen, air, and any combinations thereof.

16. A composition for killing insects, comprising: between about 0.05 and about 0.5% by weight of transfluthrin, between about 0.05 and about 0.5% by weight of prallethrin, between about 0.05 and about 0.5% by weight of cypermethrin,
between about 10 and about 90% by weight of a petroleum distillate solvent or an isoparaffinic hydrocarbon solvent or both, and
between about 10 and about 80% by weight of a propellant;
wherein the transfluthrin, the prallethrin, and the cypermethrin are the only pyrethroids in the composition.

17. A method of killing insects, the method comprising:
providing the composition of claim 1 in a dispenser which dispenses the composition at a rate of between about 2.0 gram/second and about 3.5 gram/second, and
spraying the composition for a duration of between about 4 and about 5 seconds.

18. The composition of claim 1, wherein: an average time to reach 90% mortality (KT90) in southern house mosquitoes when using the composition of claim 1 is about 2.75 minutes at a spray duration of about 0.9 seconds, and an average time to reach 90% mortality (KT90) in American cockroaches when using the composition of claim 1 is about 177 seconds at a spray duration of about 0.9 seconds.

19. The composition of claim 1, wherein: an average time to reach 90% mortality (KT90) in southern house mosquitoes when using the composition of claim 1 is about 2.75 minutes at a spray duration of about 0.9 seconds, and an average time to reach 90% mortality (KT90) in German cockroaches when using the composition of claim 1 is about 27.6 seconds at a spray duration of about 0.9 seconds.

20. The composition of claim 1, wherein:
the propellant is present at a concentration in the composition such that the composition is discharged as a foam.

21. The composition of claim 10, wherein:
the propellant is present at a concentration in the composition such that the composition is discharged as a foam.

22. The composition of claim 16, wherein:
the propellant is present at a concentration in the composition such that the composition is discharged as a foam.

* * * * *